US010531841B2

(12) United States Patent
Merritt et al.

(10) Patent No.: US 10,531,841 B2
(45) Date of Patent: Jan. 14, 2020

(54) DEVICES, SYSTEMS, AND METHODS AND ASSOCIATED DISPLAY SCREENS FOR ASSESSMENT OF VESSELS WITH MULTIPLE SENSING COMPONENTS

(71) Applicant: Volcano Corporation, San Diego, CA (US)

(72) Inventors: Fergus Merritt, Escondido, CA (US); Andrew Tochterman, Carlsbad, CA (US); David Anderson, Temecula, CA (US)

(73) Assignee: VOLCANO CORPORATION, San Diego, CA (US)

( * ) Notice: Subject to any disclaimer, the term of this patent is extended or adjusted under 35 U.S.C. 154(b) by 1075 days.

(21) Appl. No.: 14/799,347

(22) Filed: Jul. 14, 2015

(65) Prior Publication Data

US 2016/0015327 A1    Jan. 21, 2016

Related U.S. Application Data

(60) Provisional application No. 62/024,901, filed on Jul. 15, 2014.

(51) Int. Cl.
*A61B 5/02* (2006.01)
*A61B 5/00* (2006.01)
*A61B 5/0215* (2006.01)

(52) U.S. Cl.
CPC .......... *A61B 5/743* (2013.01); *A61B 5/02158* (2013.01); *A61B 5/7278* (2013.01)

(58) Field of Classification Search
CPC ... A61B 5/026; A61B 5/0261; A61B 5/02154; A61B 5/743; A61B 5/489; A61B 5/02158
See application file for complete search history.

(56) References Cited

U.S. PATENT DOCUMENTS

| 4,691,709 A | 9/1987 | Cohen |
| 6,354,999 B1 | 3/2002 | Dgany |

(Continued)

FOREIGN PATENT DOCUMENTS

| EP | 2298162 A1 | 3/2001 |
| WO | WO2000/53081 | 9/2000 |

(Continued)

OTHER PUBLICATIONS

International Preliminary Report on Patentability, Written Opinion of the ISA, and International Search Report for PCT patent application No. PCT/US2012/050015 filed Jan. 6, 2012, published as WO2012/093260, 23 pages.

(Continued)

*Primary Examiner* — Christian Jang

(57) ABSTRACT

Devices, systems, and methods for visually depicting a vessel and evaluating treatment options are disclosed. The methods can include obtaining proximal pressure measurements from a proximal pressure sensing component positioned within a vessel of a patient; obtaining distal pressure measurements from multiple pressure sensing components positioned within the vessel of the patient, wherein the multiple pressure sensing components are positioned distal of the proximal pressure sensing component and are spaced along a length of the vessel; and outputting a screen display having a visual representation of the proximal and distal pressure measurements.

20 Claims, 7 Drawing Sheets

(56) References Cited

U.S. PATENT DOCUMENTS

| | | |
|---|---|---|
| 7,930,014 B2 | 4/2011 | Huennekens |
| 8,290,228 B2 | 10/2012 | Cohen et al. |
| 8,781,193 B2 | 7/2014 | Steinberg |
| 2004/0176683 A1 | 9/2004 | Whitin |
| 2006/0052700 A1 | 3/2006 | Svanerudh |
| 2006/0106321 A1 | 5/2006 | Lewinsky et al. |
| 2007/0060822 A1 | 3/2007 | Alpert et al. |
| 2007/0100239 A1 | 5/2007 | Nair |
| 2008/0139951 A1 | 6/2008 | Patangay |
| 2008/0221439 A1 | 9/2008 | Iddan et al. |
| 2008/0221440 A1 | 9/2008 | Iddan et al. |
| 2008/0221442 A1 | 9/2008 | Tolkowsky |
| 2010/0234698 A1 | 9/2010 | Manstrom |
| 2013/0046190 A1 | 2/2013 | Davies |
| 2014/0180032 A1* | 6/2014 | Millett ............... A61B 5/02007 600/301 |
| 2014/0187920 A1* | 7/2014 | Millett ................. A61B 6/5247 600/424 |
| 2015/0025330 A1 | 1/2015 | Davies et al. |
| 2015/0025398 A1 | 1/2015 | Davies et al. |

FOREIGN PATENT DOCUMENTS

| | | |
|---|---|---|
| WO | WO2001/13779 A2 | 3/2001 |
| WO | WO2008/107905 | 9/2008 |
| WO | WO2012/093260 | 7/2012 |
| WO | WO2012/093266 | 7/2012 |
| WO | WO2013/028612 A2 | 2/2013 |

OTHER PUBLICATIONS

International Preliminary Report on Patentability, Written Opinion of the ISA, International Search Report for PCT patent application No. PCT/GB2012/050024, filed Jan. 6, 2012 and published as WO2012/093266, 25 pages.

International Preliminary Report on Patentability. Written Opinion of the ISA, and International Search Report for PCT patent application No. PCT/US2012/051566 filed Aug. 20, 2012, published as WO2013/028612, 14 pages.

J.E. Davies: Evidence of a Dominant Backward-Propagating "Suction" Wave Responsible for Diastolic Coronary filling in Humans, Attenuated in Left Ventricular Hypertrophy, Circulation, vol. 113, No. 14, Apr. 11, 2006, pp. 1768-1778, XP55006653, ISSN: 0009-7322, DOI: 10.1161/CIRCULATIONAHA.105.603.050.

International Preliminary Report on Patentability. Written Opinion of the ISA, and International Search Report for PCT patent application No. PCT/IL/2008/000316 filed Jan. 6, 2012, published as WO2008/107905 dated Sep. 12, 2008, 88 pages.

\* cited by examiner

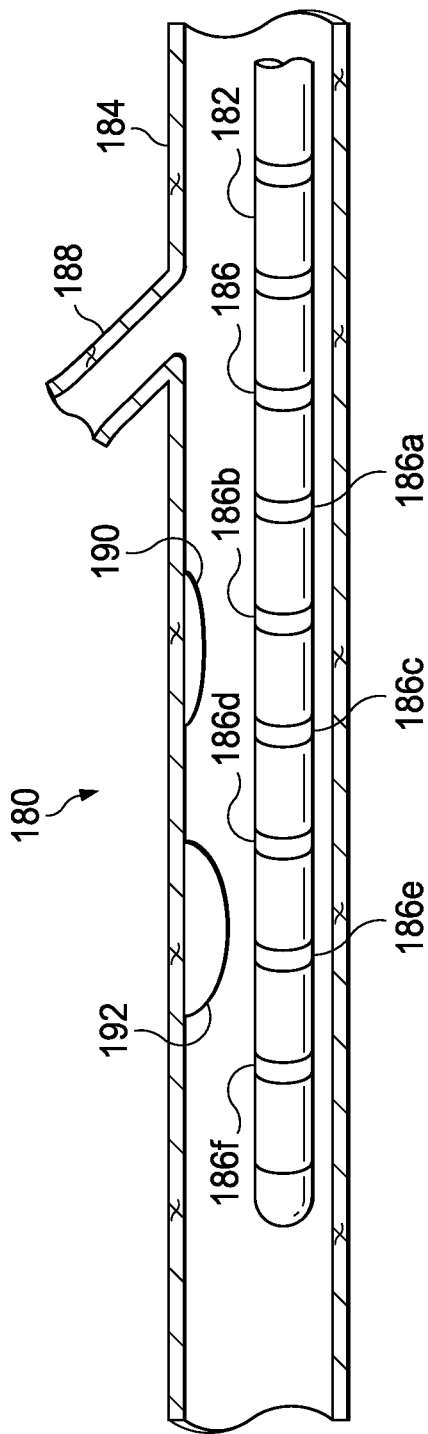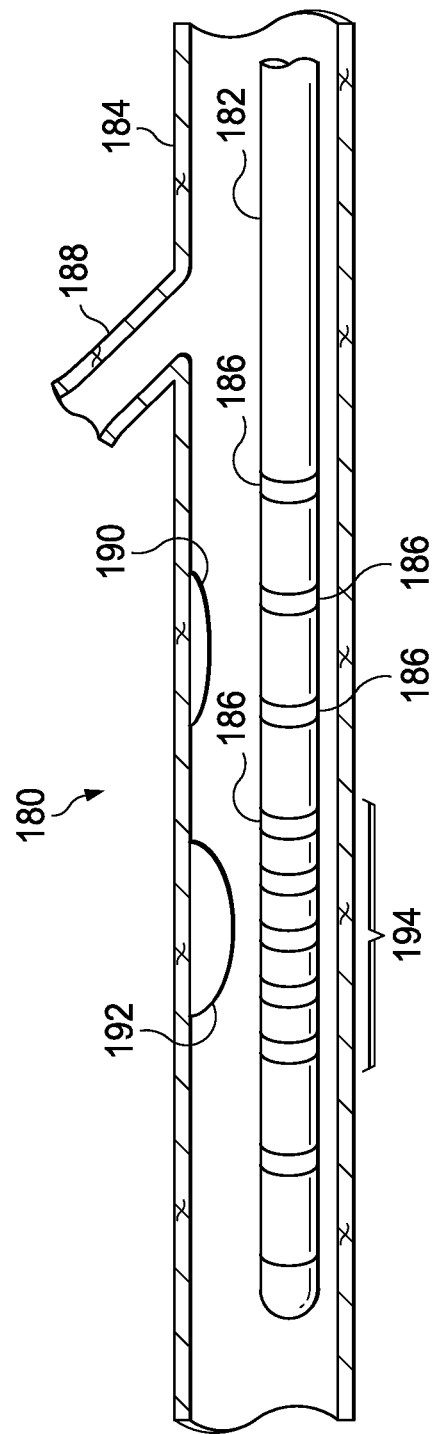

DEVICES, SYSTEMS, AND METHODS AND ASSOCIATED DISPLAY SCREENS FOR ASSESSMENT OF VESSELS WITH MULTIPLE SENSING COMPONENTS

CROSS REFERENCE TO RELATED APPLICATIONS

The present application claims priority to and the benefit of the U.S. Provisional Patent Application No. 62/024,901, filed Jul. 15, 2014, which is hereby incorporated by reference in its entirety.

TECHNICAL FIELD

The present disclosure relates generally to the assessment of vessels and, in particular, the assessment of the severity of a blockage or other restriction to the flow of fluid through a vessel using multiple sensing components on one or more intravascular devices. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance predominantly by reducing the microcirculation resistance associated with the systolic portion of the heart cycle to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries that do not require the administration of hyperemic agents. Further, there remains a need for improved devices, systems, and methods for providing visual depictions of vessel that allow assessment of the vessel and, in particular, any stenosis or lesion of the vessel. Further still, there remains a need for improved devices, systems, and methods that eliminate the need to pullback or otherwise move an intravascular device through a vessel to assess stenosis severity along the length of the vessel. In that regard, many vessels or portions thereof are difficult to access. Once accessed, it is desirable to maintain the intravascular device in the region of interest within the vessel so that the user is not faced with the challenge of reaccessing the desired portion of the vessel.

SUMMARY

Embodiments of the present disclosure are configured to assess the severity of a blockage in a vessel and, in particular, a stenosis in a blood vessel. In some particular embodiments, the devices, systems, and methods of the present disclosure are configured to utilize multiple sensing components on one or more intravascular devices to allow assessment of the vessel and, in particular, any stenosis or lesion of the vessel based on the data obtained by the multiple sensing components. In some implementations, data is obtained by the sensing components at different locations along the length of the vessel to simulate the pullback of a single sensing component through the vessel. Screen displays are also provided that convey the data obtained by the sensing components in a manner that allows a user to evaluate the severity of the blockage(s) in the vessel.

In some embodiments, a method of evaluating a vessel of a patient comprises: obtaining proximal pressure measurements from a proximal pressure sensing component positioned within a vessel of a patient; obtaining distal pressure measurements from multiple pressure sensing components positioned within the vessel of the patient, wherein the multiple pressure sensing components are positioned distal of the proximal pressure sensing component and are spaced along a length of the vessel; and outputting a screen display having a visual representation of the proximal and distal pressure measurements.

In some embodiments, a method of evaluating a vessel of a patient comprises obtaining proximal pressure measurements from a proximal pressure sensing component positioned within a vessel of a patient; obtaining distal pressure measurements from multiple distal pressure sensing components positioned within the vessel of the patient, wherein the multiple distal pressure sensing components are positioned distal of the proximal pressure sensing component and are spaced along a length of the vessel; obtaining an angiographic image of the vessel while the multiple distal pressure sensing components are positioned within the vessel; correlating at least the distal pressure measurements from the multiple distal pressure sensing components to locations on the angiographic image; and outputting an enhanced angiographic image of the vessel on a display, the enhanced angiographic image including the angiographic image overlaid with visualizations representing at least the distal pressure measurements at the correlated locations.

In some embodiments, systems configured to facilitate performance of the methods of the present disclosure are provided. Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIGS. 5A and 5B show diagrammatic schematic views of a medical sensing device used in a procedure according to some embodiments of the present disclosure.

DETAILED DESCRIPTION

Figure 1:
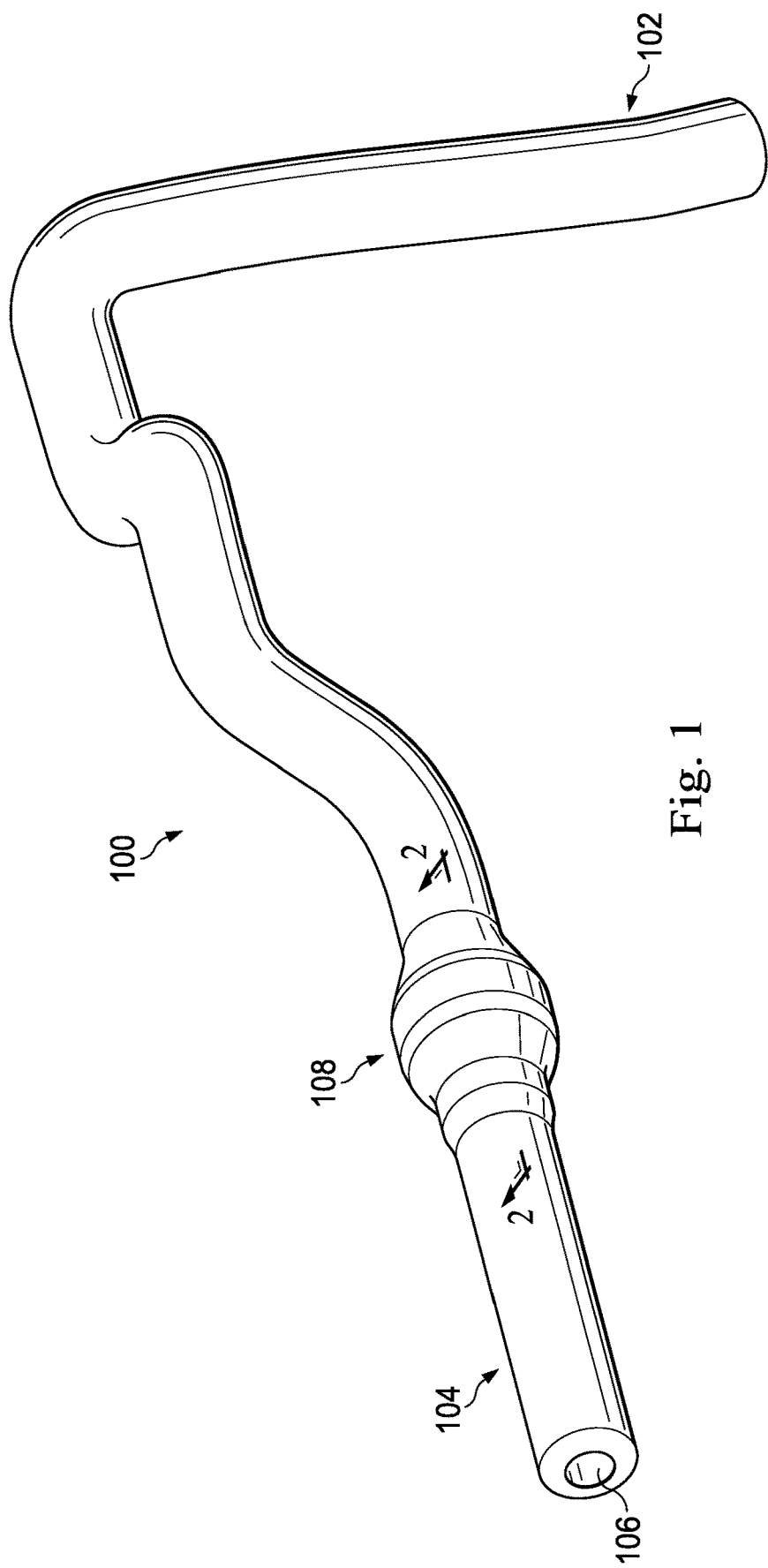
FIG. 1 shows a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
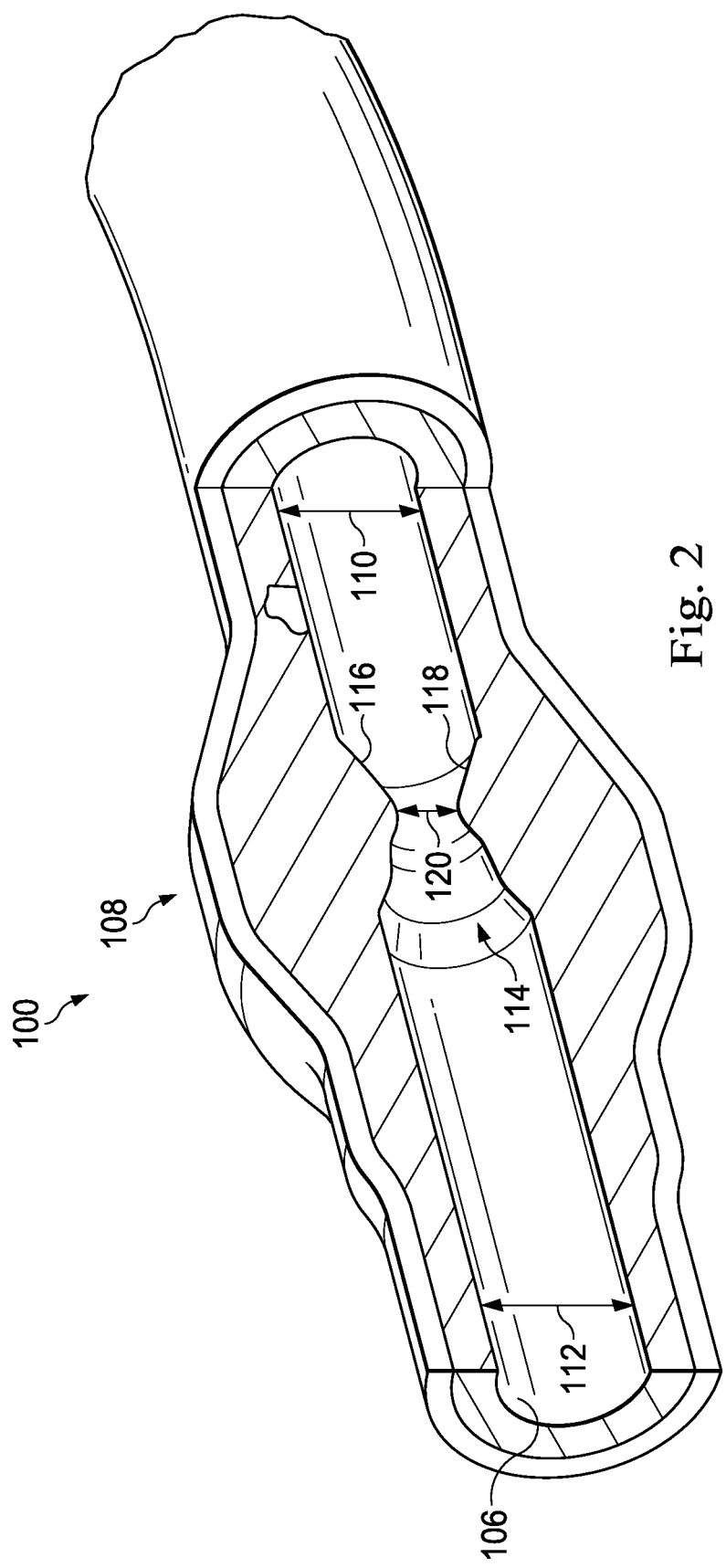
FIG. 2 shows a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
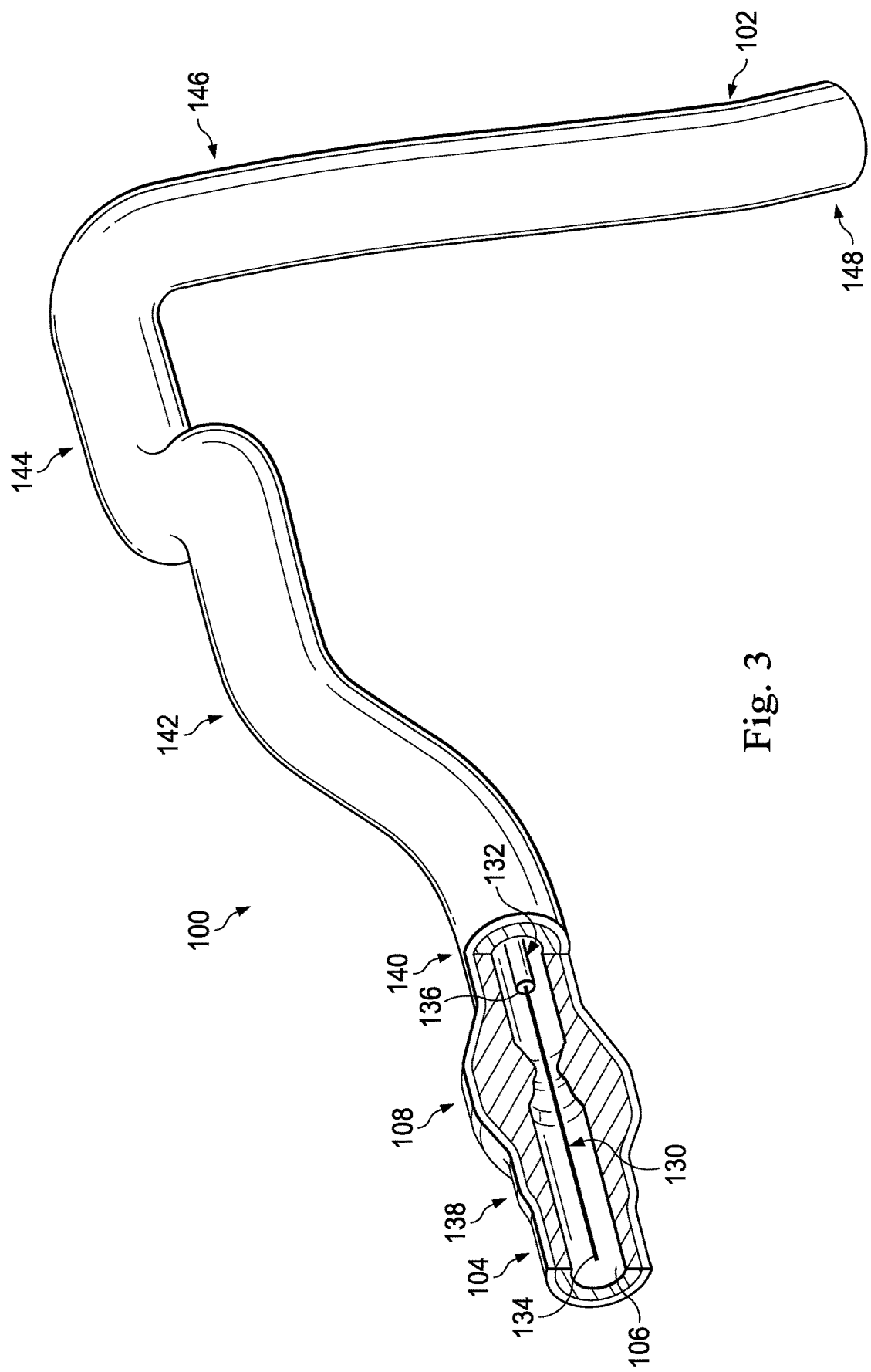
FIG. 3 shows a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In some implementations, one or both of instruments 130 and 132 are multi-sensor instruments as discussed in greater detail with respect to FIGS. 5A and 5B below. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132. Finally, instruments 130 and 132 may be used in combination with one or more other instruments.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

Figure 4:
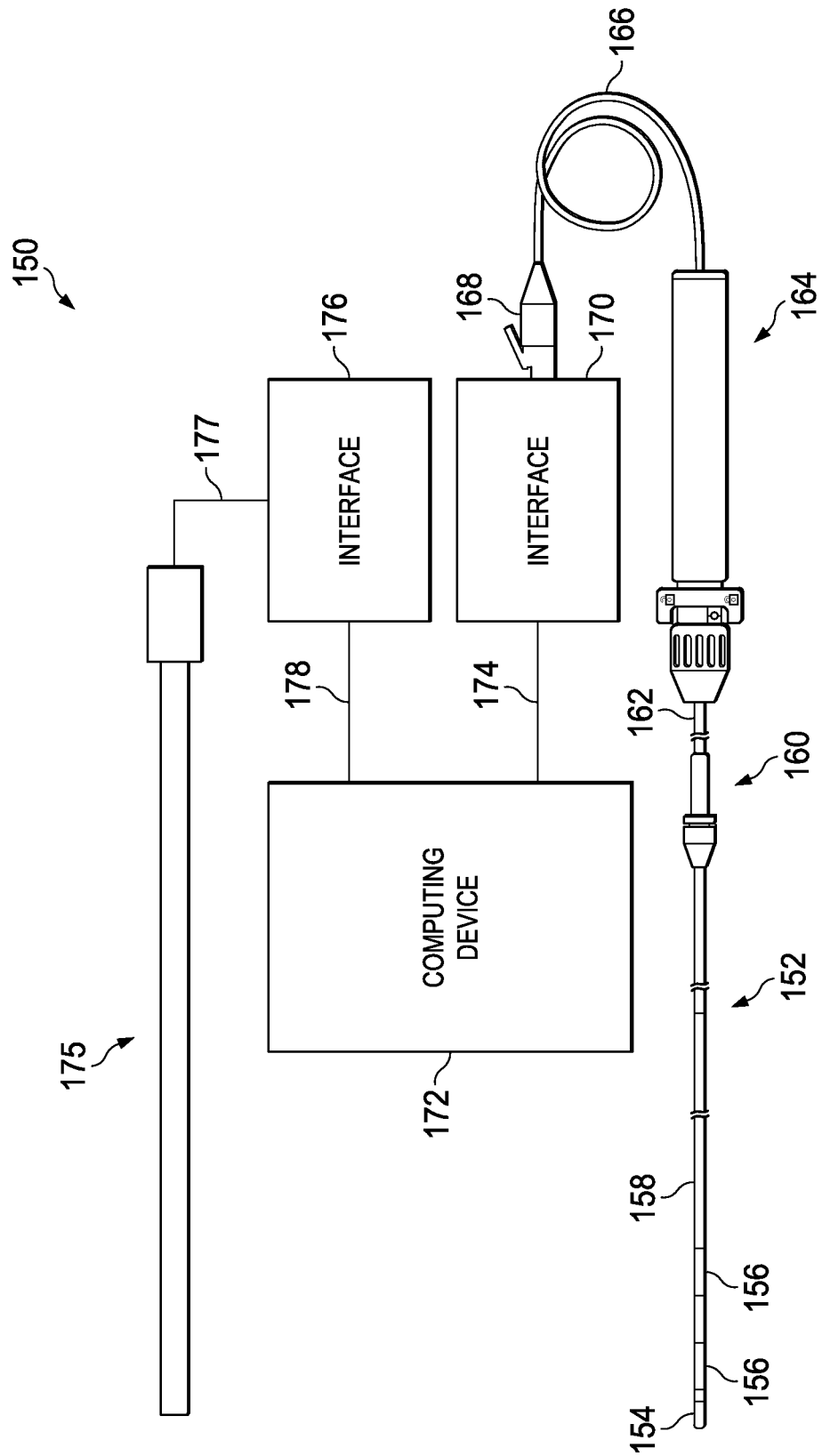
FIG. 4 shows a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132. In the illustrated embodiment, the instrument 152 is a guide wire having a distal portion 154 with multiple sensing components 156 positioned adjacent the distal portion. Generally, the instrument 152 may include any number of sensing components 156, but in some embodiments has between 2 and 20 sensing components, between 2 and 10 sensing component, or between 2 and 5 sensing components. Further, the sensing components 156 may be equally or variably spaced along the length of the instrument 152. In that regard, the multiple sensing components 156 may be arranged as discussed with respect to FIGS. 5A and 5B below. In that regard, in some implementations a marker, such as a radiopaque marker, indicates the location of each of the sensing components 156 on the instrument 152. The marker can be utilized to co-register the data obtained by each of the sensing components 156 with other data/images of the vessel as discussed below. In some implementations, the sensing components 156 are not identified with a marker. However, in some implementations the sensing components 156 are in a fixed and/or known positional relationship with respect to one or more markers of the instrument 152 such that the relative positions of the sensing components 156 can be determined based on the location of the marker(s), which can be used in a similar manner to co-register the data from the sensing components 156 with other data/images related to the vessel.

The multiple sensing components 156 are configured to obtain diagnostic information about the vessel. In the illustrated embodiment, the sensing components 156 include at least one pressure sensor configured to monitor a pressure within a lumen in which the instrument 152 is positioned. A shaft 158 extends proximally from the distal portion 154. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the multiple sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Referring now to FIGS. 5A and 5B, shown therein are diagrammatic schematic views of a medical sensing device used in a procedure 180 according to some embodiments of the present disclosure. With reference first to FIG. 5A, an instrument 182 of the medical sensing device is advanced into a vessel 184. The instrument 182 can be similar to instruments 130, 132, and 152. In that regard, the instrument 182 incorporates sensors 186 (including sensors 186a-f) in the distal portion of the instrument 182. The sensors 186 correspond to one or more sensing modalities such as pressure, flow, imaging (IVUS, FL-IVUS, OCT, etc.) and/or other suitable sensing modalities. Vessel 184 represents fluid filled or surrounded structures, both natural and man-made, within a living body and can include for example, but without limitation, structures such as: organs including the liver, heart, kidneys, gall bladder, pancreas, lungs; ducts; intestines; nervous system structures including the brain, dural sac, spinal cord and peripheral nerves; the urinary tract; as well as valves within the blood or other systems of the body. In addition to natural structures, instrument 182 may be used to examine man-made structures such as, but without limitation, heart valves, stents, shunts, filters and other devices positioned within the body, for example, a guide wire or guide catheter.

Many cardiovascular structures of interest cannot be accurately located using external means. In many other applications, while the location of the both structure of interest and the instrument 182 can be determined generally, achieving the proper alignment of the two proves challenging. Therefore, it may be advantageous to use the array of sensors 186 arranged along the longitudinal length of the instrument 182 to determine the location of the structure of interest within the vessel. In the illustrated embodiment, the instrument 182 is advanced into the vessel 184 until it is in the general area of structures 188, 190, and 192. In various applications, structures of interest include bifurcations, stenoses, plaques, vascular dissections, lesions, stents, and/ or other suitable venous morphology. Once in position, a series of measurements are obtained from which the vascular structure can be detected. In some instances, the locations of the sensors 186 at the time data is obtained is co-registered with images of the vessel. In some implementations, a representation of the data obtained by the sensors 186 is overlaid onto the image of the vessel such that a user can visualize the data in the context of the vessel. An example of such a co-registered display is provided and discussed in greater detail with respect to FIG. 7 below.

In some embodiments, sensors 186 are pressure sensors, and a series of fractional flow reserve (FFR) ratios, instantaneous wavefree ratios (iFR), and/or compensated Pd/Pa ratios are calculated. FFR is a currently accepted technique for assessing the severity of a stenosis in a blood vessel, including ischemia-causing lesions, and may be used to determine other types of vascular structures. FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Further measurements such as Instant Wave-Free Ratio™ Functionality data (iFR® Functionality) (both trademarks of Volcano Corp.) and those disclosed in U.S. patent application Ser. No. 13/460,296 filed Apr. 30, 2012 published as 2013/0046190 on Feb. 21, 2013, entitled "DEVICES, SYSTEMS, AND METHODS FOR ASSESSING A VESSEL," hereby incorporated by reference in its entirety, which discloses the use of pressure ratios that are available without application of a hyperemic agent, are also suitable for use in some embodiments. Compensated Pd/Pa ratios can be suitable for estimating iFR®, FFR, and/or other accepted diagnostic pressure ratios as disclosed in U.S. Provisional Patent Application No. 62/024,005, filed Jul. 14, 2014 and entitled "DEVICES, SYSTEMS, AND METHODS FOR TREATMENT OF VESSELS," which is hereby incorporated by reference in its entirety. From the iFR® and/or FFR data, structures such as stenoses can be inferred. For example, in some embodiments, an FFR below a threshold (e.g., 0.80) suggests that a structure such as a stenosis lies between the proximal and the distal sensors 186. Thus, the location and severity of each of the stenoses of a vessel can be inferred from the known location of the sensors 186 on either side of where the FFR measurement drops below the threshold.

In other exemplary embodiments, one or more of the sensors 186 is an IVUS transducer or OCT transceiver utilized to take cross-sectional or forward-looking views of the vessel 184 along the length of the instrument 182. In such embodiments, the location of vascular structures (e.g., structures 188, 190, and 192) may be determined by examining differences in images across sensors, by a tissue characterization process, and/or by other diagnostic examination of the data.

The data collected by the sensors 186 can be utilized for diagnostic purposes. For example, in one embodiment, the sensors 186 include pressure sensors, and a series of pressure ratio determinations are taken along the length of the member 182. In the example, the data indicates multiple plaque stenoses (e.g., structures 190 and 192). Therefore, a pressure ratio is calculated to determine the combined effect using a proximal sensor positioned proximal to all of the plaques (e.g., sensor 186a or a sensor of a separate instrument) and a distal sensor positioned distal to all of the plaques (e.g., sensor 186f). Similarly, a pressure ratio can be calculated to separate the effect of structure 192 from structure 190 by using a distal sensor positioned distal of structure 190, but proximal of structure 192 (e.g., sensor 186d).

Further, pressure ratios can be calculated for each sensor 186 over time to determine the individual effect of each stenosis along the length of the vessel 184 and/or relative changes in vessel health between each sensor 186. In this way, the operator can distinguish stenoses that are individually benign but collectively acute, and can determine which obstructions have the largest overall contribution. In some instances, the pressure measured by each sensor 186 is compared to an aortic pressure measurement obtained by a separate pressure-sensing catheter. In some implementations, the instrument 182 is used to perform a virtual pullback. In response to a user command, data is collected from the sensors 186 in sequence over time. Stepping through the sensors 186 in order of location simulates a pullback of a single sensor through the vessel 184 without actually withdrawing or moving the location of the instrument 182 within the vessel. This allows the subsequent measurements of the simulated pullback to be performed without repositioning the device.

In further exemplary embodiments, other combinations of sensors 186 and modalities are used to locate and/or evaluate vascular structures, and one of skill in the art will recognize that the location and/or severity of a vascular structure can be determined using a variety of sensors 186 and modalities without departing from the spirit of the present disclosure.

Referring now to FIG. 5B, the instrument 182, the incorporated sensors 186, and the vessel 184 are substantially similar to those disclosed with reference to FIG. 5A. However, the instrument 182 also includes a detailed sensing region 194. Once a structure of interest is located, the detailed sensing region 194 may be used to examine the structure. The detailed sensing region 194 is maneuvered into position adjacent to the structure (e.g., structure 192), and data is collected using the associated sensors 186. In the illustrated embodiment, the detailed sensing region 194 has tighter sensor spacing than the remainder of the instrument 182. In addition or in the alternative, the detailed sensing region 194 may incorporate different types of sensors that correspond to different modalities or sets of modalities. In some embodiments, the sensors of the detailed sensing region have a higher sensing resolution along the axial length of the instrument 182 than other sensors of the instrument 182. In various further embodiments, the detailed sensing region 194 has other sensing differences as compared to the remainder of the instrument 182.

Figure 6:
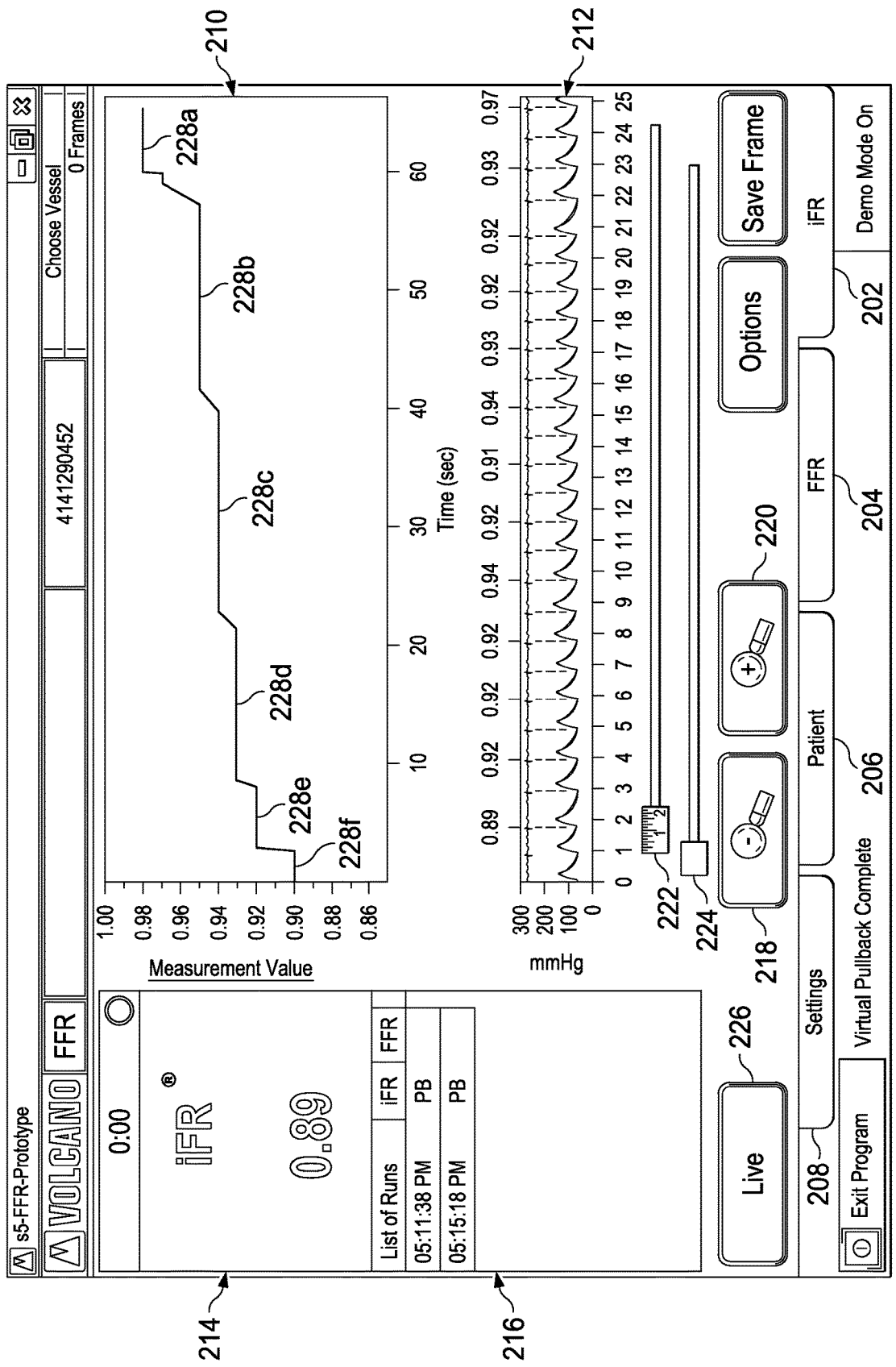
FIG. 6 shows a screen display according to an embodiment of the present disclosure.

Referring now to FIG. 6, shown therein is a screen display 200 according to an embodiment of the present disclosure. The screen display 200 includes multiple tabs, including an iFR tab 202, an FFR tab 204, a patient tab 206, and a settings tab 208. In FIG. 6, the iFR tab 202 has been selected and displayed to a user. As shown, the iFR tab 202 includes a graph 210 and a corresponding a pressure waveform plot 212 based on the data obtained using multiple sensing components. The screen display 200 also includes a window 214 that shows a calculated pressure ratio (e.g., FFR, iFR, or otherwise). The screen display 200 also includes a window 216 showing the runs or virtual pullbacks available for display to the user. In the illustrated embodiment, two different runs or virtual pullbacks are available and identified by a corresponding time stamp. In that regard, a user can select the desired run or virtual pullback from the window 216 and the data shown in the graph 210 and pressure waveform plot 212 will update accordingly.

The screen display 200 also includes zoom buttons 218, 220 that allow a user to zoom out or in, respectively, on the graph 210 and the pressure waveform plot 212. To this end, the screen display 200 includes a ruler 222 showing the relative scale of the graph 210 and the pressure waveform plot 212. In some instances, the ruler 222 provides a dimensional scale of the graphical display of the graph 210 and/or the pressure waveform plot 212 relative to the vessel length and/or the pullback length. The scale of the ruler 222 automatically updates in response to selective actuation of the zoom buttons 218, 220 in some implementations.

The screen display 200 also includes a slider 224. The slider 224 allows the user to move along the length of the vessel and/or the corresponding virtual pullback data. For example, in some instances the left end of the slider 224 corresponds to the beginning of the pullback (i.e., data from the first sensing component) and the right end of the slider corresponds to the end of the pullback (i.e., data from the last sensing component). By moving the slider 224 between the first and second ends, a user can see corresponding portions of the pressure data in the graph 210 and the pressure waveform plot 212. Accordingly, a user can focus on certain portions of the vessel and virtual pullback data using the zoom buttons 218, 220 in combination with the slider 224. In some instances, the numerical value of the pressure ratio displayed in window 214 is updated based on the position of the slider. In that regard, in some instances the numerical value of the pressure ratio displayed in window 214 is based solely on the pressure data being displayed in the graph 210 and the pressure waveform plot 212. However, in other instances the numerical value of the pressure ratio displayed in window 214 is based one of or a combination of the pressure data being displayed in the graph 210 and the pressure waveform plot 212 and pressure data not displayed in the graph 210 and the pressure waveform plot 212.

In that regard, the graph 210 and pressure waveform plot 212 of screen display 200 illustrate aspects of pressure measurements obtained by multiple sensing components of one or more instruments positioned within the vessel. In that regard, the sensing components are maintained in fixed or stationary location during the procedure. In some instances the pressure measurements are representative of a pressure ratio between a sensing component at one location within the vessel and a sensing component at another location within the vessel. In some implementations, a sensing component at a reference location is utilized to compare the pressure measurements from the other sensing components. For example, in some instances a proximal pressure measurement is obtained at a fixed location within the vessel or aorta and the pressure measurements from the other sensing components are compared to the reference proximal pressure measurement. For clarity in understanding the concepts of the present disclosure, this arrangement is utilized to describe many of the embodiments of the present disclosure. However, it is understood that the concepts are equally applicable to other arrangements.

The pressure differential between two pressure measurements within the vessel can be calculated as a ratio of the two pressure measurements (i.e., one pressure measurement divided by the other pressure measurement) in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances.

In some embodiments a diagnostic window is selected using one or more of the techniques described in U.S. patent application Ser. No. 13/460,296, filed Apr. 30, 2012 published as 2013/0046190 on Feb. 21, 2013 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In the illustrated embodiment of FIG. 6, the graph 210 shows the pressure ratio over time. In particular, the graph 210 shows the pressure ratio calculated over the time of a virtual pullback. More specifically, the graph 210 shows an iFR pressure ratio value during a virtual pullback, where multiple sensing components were utilized to obtain pressure data at different locations along the length of the vessel over time. In that regard, the iFR pressure ratio may be calculated as described in one or more of PCT Patent Application Publication No. WO 2012/093260, filed Jan. 6, 2012 and titled "APPARATUS AND METHOD OF CHARACTERISING A NARROWING IN A FLUID FILLED TUBE," PCT Patent Application Publication No. WO 2012/093266, filed Jan. 6, 2012 and titled "APPARATUS AND METHOD OF ASSESSING A NARROWING IN A FLUID FILLED TUBE," U.S. patent application Ser. No. 13/460,296, filed Apr. 30, 2012 published as U.S. Patent Application Publication No. 2013/0046190 on Feb. 21, 2013 and titled "DEVICES, SYSTEMS, AND METHODS FOR ASSESSING A VESSEL," PCT Patent Application Publication No. WO 2013/028612, filed Aug. 20, 2012 and titled "DEVICES, SYSTEMS, AND METHODS FOR VISUALLY DEPICTING A VESSEL AND EVALUATING TREATMENT OPTIONS," U.S. Provisional Patent Application No. 61/856,509, filed Jul. 19, 2013 now U.S. patent application Ser. No. 14/335,603 filed Jul. 18, 2014 and published as U.S. Patent Application Publication No. 2015/0025330 on Jan. 22, 2015 and titled "DEVICES, SYSTEMS, AND METHODS FOR ASSESSMENT OF VESSELS," and U.S. Provisional Patent Application No. 61/856,518, filed Jul. 19, 2013 now U.S. patent application Ser. No. 14/335,680 filed Jul. 18, 2014 and published as U.S. Patent Application Publication No. 2015/0025398 on Jan. 22, 2015 and titled "DEVICES, SYSTEMS, AND METHODS FOR ASSESSING A VESSEL WITH AUTOMATED DRIFT CORRECTION," each of which is hereby incorporated by reference in its entirety.

It is understood that the graph 210 can illustrate the pressure ratio and/or the underlying pressure measurements obtained by the multiple sensing components in any suitable way. Generally speaking, the representation of the data in graph 210 can be utilized to identify gradients/changes in the pressure ratio and/or the underlying pressure measurements that can be indicative of a significant lesion in the vessel. In that regard, the visual representation of the data can include the pressure measurement(s); a ratio of the pressure measurements; a difference in the pressure measurements; a gradient of the pressure measurement(s), the ratio of the pressure measurements, and/or the difference in the pressure measurements; first or second derivatives of the pressure measurement(s), the ratio of the pressure measurements, and/or the difference in the pressure measurements; and/or combinations thereof. Other examples of suitable ways of representing data from pressure sensors suitable for use with the multiple sensor arrangements of the present disclosure are provided in U.S. Patent Application No. 61/942,338, filed Feb. 20, 2014, which is hereby incorporated by reference in its entirety.

Likewise, the pressure waveform plot 212 shows the corresponding pressure data. In that regard, the pressure waveform plot 212 can include the pressure waveform for the active pressure sensing device at a given time during the virtual pullback, the pressure waveform for the reference pressure sensing device, the pressure waveform for non-active pressure sensing devices at a given time during the pullback (e.g., a sensing device not in current use as part of the virtual pullback data acquisition sequence), and/or any combination thereof. In the illustrated embodiment, the pressure waveform plot 212 includes the pressure waveforms for the active pressure sensing device at a given time during the virtual pullback and the pressure waveform for the reference pressure sensing device. The pressure waveform plot 212 can be augmented to highlight or otherwise accentuate the pressure data corresponding to the diagnostic window utilized for the pressure ratio calculations as described in U.S. Patent Application No. 61/942,338, filed Feb. 20, 2014, which is hereby incorporated by reference in its entirety.

As shown in FIG. 6, the screen display 200 includes a button 226 indicating that the data is being displayed in a "Live" mode, which indicates that the screen display 200, including graph 210, pressure waveform plot 212, and/or the window 214, is being updated in real time as a procedure is being performed. In other instances, the button 226 of the screen display 200 will indicated that it is in "Playback" or "Review" mode, which indicates that the screen display 200 is showing data obtained previously. With respect to the "Live" mode, it should be noted that the determination of the diagnostic window and/or the calculation of the pressure differential are performed in approximately real time or live to identify the diagnostic window of the heartbeat cycle and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In that regard, the coloring and/or other visually distinguishing aspect of the pressure differential measurements depicted in graph 210 and/or window 214 of the screen display 200 of FIG. 6 are configured based on the threshold value in some instances. For example, a first color (e.g., green, white, or otherwise) can be utilized to represent values well above the threshold value (e.g., where the threshold value is 0.80 on a scale of 0.00 to 1.00, values above 0.90), a second color (e.g., yellow, gray, or otherwise) can be utilized to represent values near but above the threshold value (e.g., where the threshold value is 0.80 on a scale of 0.00 to 1.00, values between 0.81 and 0.90), and a third color (e.g., red, black, or otherwise) can be utilized to represent values equal to or below the threshold value (e.g., where the threshold value is 0.80 on a scale of 0.00 to 1.00, values of 0.80 and below). Further, in some instances the graph 210 includes one or more horizontal lines or other depictions representing the threshold value(s). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

In the illustrated embodiment of FIG. 6, graph 210 is depicted based on pressure measurements obtained from multiple distal pressure sensing components over time as part of a virtual pullback. For clarity in illustration, reference will be made to the instrument 182 of FIG. 5a and its sensors

186a-186f. In that regard, graph 210 can be understood to include sections 228a-228f that correspond to the data obtained from sensors 186a-186f, respectively. As a result of the stepped or sequenced data acquisition associated with the virtual pullback, the graph 210 has a corresponding stepped profile across the sections 228a-228f.

Figure 7:
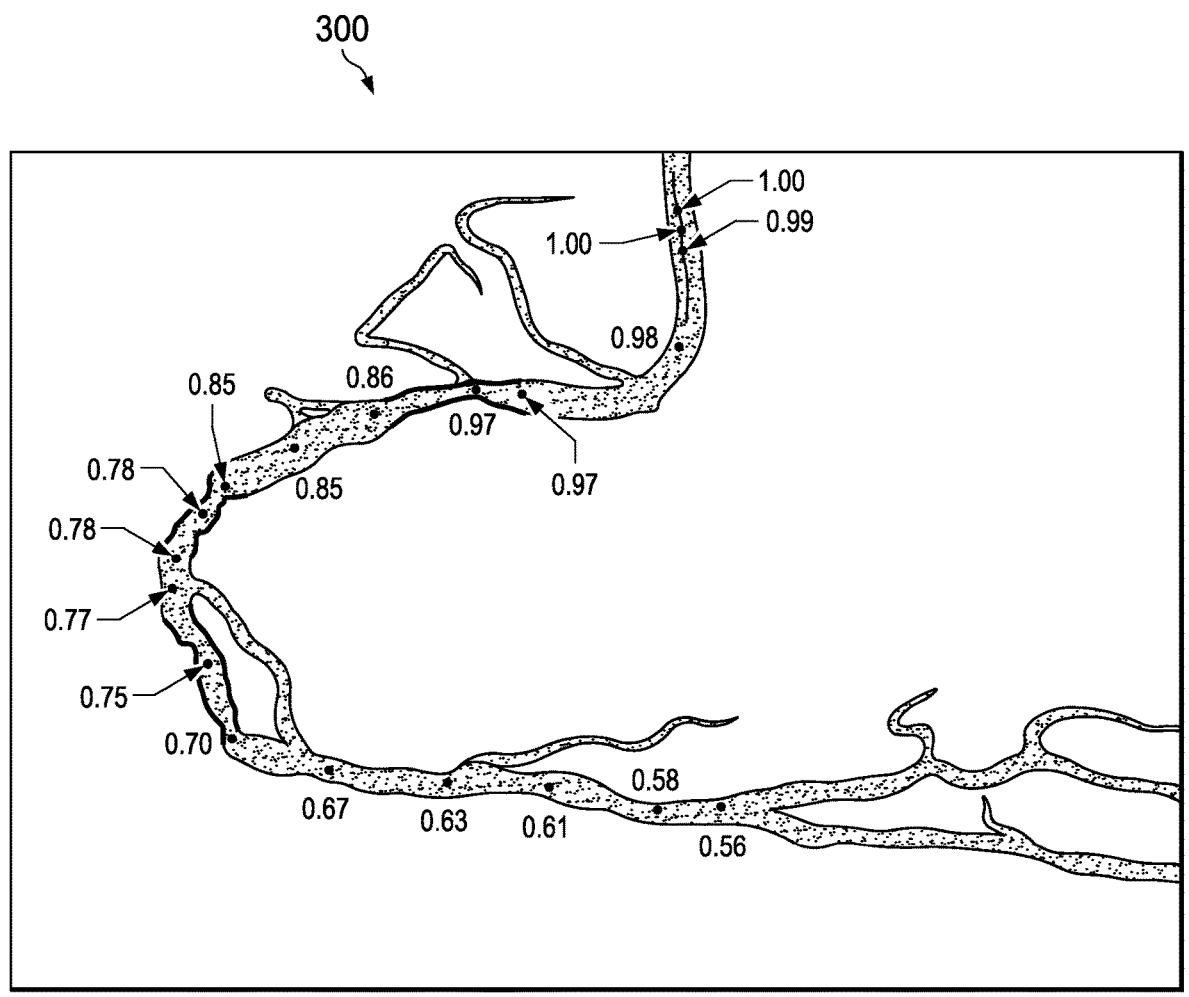
FIG. 7 shows a portion of a screen display according to another embodiment of the present disclosure.

Referring now to FIG. 7, shown therein is a portion of a screen display according to another embodiment of the present disclosure. In particular, shown therein is an enhanced angiographic image 300 of a vessel based on intravascular measurements according to an embodiment of the present disclosure. It is understood that the angiographic image can be a two dimensional angiographic image, a three dimensional angiographic image, and a computed tomography angiographic (CTA) image. It is also understood that the concepts described below can also be applied to other imaging techniques, both external (fluoroscopy, CT, etc.) and internal (IVUS, OCT, etc.).

As shown, the intravascular physiological measurements are overlaid onto the angiographic image based on the locations of the sensing component(s) of the one or more intravascular instruments when the intravascular data is obtained. As shown in FIG. 7, angiographic images of vessels can be annotated with one or more visualizations configured to assist in identifying one or more lesions and/or stenoses, and/or assess the severity thereof. The visualizations are based on the physiology values obtained from an instrument (e.g., instrument 130, 132, 152, 182, etc.) as the instrument is positioned within the vessel. For example, FIG. 7 illustrates pressure ratio calculations (such as FFR or iFR) at different points along the length of the vessel. The vessel can be colorized and/or otherwise visualized using a heat map that illustrates changes in pressure measurements obtained as the instrument is moved through the vessel. In this manner, the colors can provide an indication of the severity of a lesion and whether it is a focal or diffuse lesion.

The enhanced angiographic images can also identify transition points or areas of the vessel wherein the physiology values between portions of the vessel change by a threshold amount. In some embodiments, the threshold amount can be fixed, while in other embodiments, the threshold amount can vary between patients. The one or more transition points can be indicated by visualizations on the angiographic image. For example, markings such as tick marks extending transversely across the vessel can be utilized to signify a transition point. In other embodiments, the markings can take different shapes (e.g., circles, squares, etc.), be in different positions relative to the vessel (beside, within, etc.), be differently sized, etc. The transition points can be representative of a boundary of a lesion or stenosis of the vessel that results in an increased or decreased pressure differential, which is illustrated by the change in color of the vessel. As a result, the visualizations of the intravascular measurements (e.g., the numerical representation of the intravascular measurements, changes in color, markings, etc.) can be utilized to both identify the location of the lesion or stenosis within the vessel and assess the severity of the lesion or stenosis.

Value indicators or numerical representations of the intravascular measurements can also be displayed on the intravascular image to indicate the location within the patient's vasculature to which the measurement corresponds. In that regard, the value indicators can be displayed proximate to the corresponding portion of the vessel or displayed further away from the corresponding portion of the vessel but with an additional visual element (e.g., an arrow, a straight line, a curved line, etc.) to indicate the location of the measurement. The color of the text or surrounding box of the intravascular data can be color coded in a similar manner to the heat map such that the color of the intravascular data in addition to the actual value can provided an indication to the user as to the severity of the lesion.

In some embodiments, the value indicators include only the value of the physiological measurement (e.g., "0.96"), while in other embodiments, the value indicators include the value and type of physiological measurement (e.g., "0.95 FFR"). In yet other embodiments, additional information, such as the time the measurement was taken, severity of the stenosis or lesion, etc. can also be provided. For example, a user may provide a user input (e.g., a selection from a drop-down menu, toggle through the available options, etc.) selecting the types of information that should be displayed in value indicators. Labels, for each of the value indicators, can also be provided. Labels can include alphabetical, numeric, and/or other symbolic characters. Labels may assist in identifying markings and/or value indicators (e.g., to distinguish between different markings/value indicators and/or to facilitate discussion of the vessel depictions). The labels can be textual indications providing the names of major and/or minor vessels or segments thereof. The labels can include alphabetical, numeric, and/or other symbolic characters. In some embodiments, labels can correspond to a listing of parts of patient's vasculature.

In some embodiments, markings and/or value indicators can be positioned automatically. The system can be configured to select locations within the vessel that are clinically significant based on the intravascular information obtained (e.g., locations where the physiology value changes significantly). In some embodiments, markings can be moved along the length of the vessel. For example, a user may provide a user input (e.g., click and drag the marking, click the marking to select it and then click a new location to which it should move, etc.) to cause movement of the markings. Value indicators may be correspondingly updated with data that is based on the new location and/or move based on new location. That is, value indicators can display diagnostic information along the length of the vessel. In this manner, a user may select a region of interest of the vessel by moving marking and/or value indicator to indicate an area of a vessel with a higher pressure differential, a lesion, and/or stenosis.

In some embodiments, visualizations to indicate a region of interest include multiple markings and a connector between the markings. In some embodiments, the markings may be individually moved and the connector corresponding lengthens or shortens to span the space between them. In other embodiments, the markings and connector are collectively translated along the vessel with a fixed length or spacing between them.

The relative position of the markings and/or value indicators of the obtained intravascular data to the vessel can be determined by co-registering the location of the sensing components of the instrument(s) at the time the data is acquired. In that regard, co-registration of the location of the intravascular instrument (and corresponding data acquisitions) with the angiographic image(s) can be completed using techniques disclosed in one or more of U.S. Pat. No. 8,290,228, titled "LOCATION-SENSITIVE CURSOR CONTROL AND ITS USE FOR VESSEL ANALYSIS," U.S. patent application Ser. No. 12/666,879, filed Dec. 28, 2009 now U.S. Pat. No. 8,781,193 issued Jul. 15, 2014 and titled "AUTOMATIC QUANTITATIVE VESSEL ANALYSIS," PCT Patent Application No. PCT/IL2008/000316, filed on Mar. 9, 2008 and published as WO2008/107905 on Sep. 12, 2008 and titled "IMAGING AND TOOLS FOR USE WITH MOVING ORGANS," U.S. patent application Ser. No. 12/075,244, filed Mar. 10, 2008 published as U.S. Patent Publication No. 2008/0221442 on Sep. 11, 2008 and titled "IMAGING FOR USE WITH MOVING ORGANS," U.S. patent application Ser. No. 12/075,214, filed Mar. 10, 2008 published as U.S. Patent Publication No. 2008/221439 on Sep. 11, 2008 and entitled "TOOLS FOR USE WITH MOVING ORGANS," and U.S. patent application Ser. No. 12/075,252, filed Mar. 10, 2008, published as U.S. Patent Publication No. 2008/0221440 on Sep. 11, 2008, and titled "IMAGING AND TOOLS FOR USE WITH MOVING ORGANS," U.S. Pat. No. 7,930,014, titled "VASCULAR IMAGE CO-REGISTRATION," and U.S. Provisional Patent Application No. 61/856,509, filed Jul. 19, 2013 now U.S. patent application Ser. No. 14/335,603 filed on Jul. 18, 2014 and published as U.S. Patent Publication No. 2015/0025330 on Jan. 22, 2015, and titled "DEVICES, SYSTEMS, AND METHODS FOR ASSESSMENT OF VESSELS," each of which is hereby incorporated by reference in its entirety.

One or more images of a vessel, the visualizations in those images, and/or the measured physiological values can be used to evaluate whether and/or how to perform a surgical procedure. For example, the measured physiological values and/or the images of the vessels, which indicate the location, extent, and severity of one or more lesions or stenoses, can be used to predict probabilities of different treatment options. The regions of interest can be used to determine how and/or where in the vasculature to intervene. For example, the location, extent, and severity of one or more lesions or stenoses, can be used to estimate the number of stents, the length of stents, etc. The physiological values can also be used to calculate a numerical or otherwise objective indication of risk/benefit, as described herein. The objective indication of risk/benefit can be used to evaluate whether and/or how to perform a surgical procedure.

It is understood that numerous other visualization techniques may be utilized to convey the information in the context of an enhanced angiographic image or other image of the vessel (including both intravascular and extravascular imaging techniques, such as IVUS, OCT, ICE, CTA, etc.) to help the user evaluate the vessel. In that regard, while the examples of the present disclosure are provided with respect to angiographic images, it is understood that the concepts are equally applicable to other types of vessel imaging techniques, including intravascular and extravascular imaging. Further, U.S. patent application Ser. No. 14/144,280, filed Dec. 30, 2013, includes additional visualization techniques that can be utilized in the context of the multiple sensor arrangements of the present disclosure.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of evaluating a blood vessel of a patient, comprising:
    obtaining proximal pressure measurements from a proximal pressure sensing component positioned within a blood vessel of a patient;
    obtaining distal pressure measurements from multiple pressure sensing components positioned within the blood vessel of the patient, wherein the multiple pressure sensing components are coupled to an intravascular catheter or guide wire that remains stationary within the blood vessel while the distal pressure measurements are obtained, wherein the multiple pressure sensing components are arranged with a fixed length between one another, wherein the multiple pressure sensing components are positioned distal of the proximal pressure sensing component; and
    outputting a screen display having visual representations of the proximal pressure measurements and the distal pressure measurements, wherein a distance between the visual representations on the screen display corresponds to the fixed length between the multiple pressure sensing components.

2. The method of claim 1, wherein the step of obtaining the distal pressure measurements includes performing a virtual pullback.

3. The method of claim 2, wherein the virtual pullback includes obtaining data from the multiple pressure sensing components in a sequence moving from a distal pressure sensing component to a proximal pressure sensing component.

4. The method of claim 2, wherein the virtual pullback includes obtaining data from the multiple pressure sensing components in a sequence moving from a proximal pressure sensing component to a distal pressure sensing component.

5. The method of claim 2, wherein the visual representation of the proximal and distal pressure measurements includes a graphical display of a pressure ratio of the obtained proximal and distal pressure measurements.

6. The method of claim 5, wherein the pressure ratio is at least one of a fractional flow reserve (FFR), an instantaneous wave-free ratio (iFR), or a compensated Pd/Pa ratio.

7. The method of claim 2, wherein the visual representation of the proximal and distal pressure measurements includes a graphical display of a change in a pressure ratio of the obtained proximal and distal pressure measurements.

8. The method of claim 1, wherein the multiple pressure sensing components utilized to obtain the distal pressure measurements are connected to a single instrument.

9. The method of claim 1, wherein the multiple pressure sensing components utilized to obtain the distal pressure measurements are connected to multiple instruments.

10. A system for evaluating a blood vessel, comprising:
    a proximal pressure sensing component sized and shaped for positioning within a blood vessel of a patient;
    multiple distal pressure sensing components sized and shaped for positioning within the blood vessel, wherein the multiple distal pressure sensing components are coupled to an intravascular catheter or guide wire, wherein the multiple distal pressure sensing components are arranged with a fixed length between one another;
    a processing unit in communication with the proximal pressure sensing component and the multiple distal pressure sensing components, the processing unit configured to:

obtain proximal pressure measurements from the proximal pressure sensing component positioned within the blood vessel of the patient;

obtain distal pressure measurements from the multiple distal pressure sensing components while the intravascular catheter or guide wire remains stationary within the blood vessel of the patient, wherein the multiple distal pressure sensing components are positioned distal of the proximal pressure sensing component; and output, to a display in communication with the processing unit, visual representations of the proximal pressure measurements and the distal pressure measurements, wherein a distance between the visual representations corresponds to the fixed length between the multiple distal pressure sensing components.

11. The system of claim 10, wherein the processing unit obtains the distal pressure measurements by performing a virtual pullback.

12. The system of claim 11, wherein the virtual pullback includes obtaining data from the multiple distal pressure sensing components in a sequence moving from a first distal pressure sensing component to a second distal pressure sensing component, the first distal pressure sensing component being positioned distal of the second distal pressure sensing component.

13. The system of claim 11, wherein the virtual pullback includes obtaining data from the multiple distal pressure sensing components in a sequence moving from a first distal pressure sensing component to a second distal pressure sensing component, the first distal pressure sensing component being positioned proximal of the second distal pressure sensing component.

14. The system of claim 11, wherein the visual representation of the proximal and distal pressure measurements includes a graphical display of a pressure ratio of the obtained proximal and distal pressure measurements.

15. The system of claim 14, wherein the pressure ratio is at least one of a fractional flow reserve (FFR), an instantaneous wave-free ratio (iFR), or a compensated Pd/Pa ratio.

16. The system of claim 11, wherein the visual representation of the proximal and distal pressure measurements includes a graphical display of a change in a pressure ratio of the obtained proximal and distal pressure measurements.

17. The system of claim 10, wherein the multiple distal pressure sensing components are connected to a single instrument.

18. The system of claim 10, wherein the multiple distal pressure sensing components are connected to multiple instruments.

19. The system of claim 10, wherein the processing unit is configured to calculate pressure ratios based on the proximal and distal pressure measurements, wherein the visual representations includes numerical values of the pressure ratios, wherein the distance between the numerical values of the pressure ratios corresponds to the fixed length between the multiple distal pressure sensing components.

20. The system of claim 10,
wherein the fixed length comprises:
a first length between two distal pressure sensing components; and
a second length between a different two distal pressure sensing components; and
wherein the distance comprises:
a first distance between two visual representations and corresponding to the first length; and
a second distance between a different two visual representations and corresponding to the second length.

* * * * *